United States Patent [19]

Kirsch et al.

[11] Patent Number: 5,134,136
[45] Date of Patent: Jul. 28, 1992

[54] 14α,17α-ETHANOESTRATRIENES

[75] Inventors: Gerald Kirsch; Henry Laurent; Rudolf Wiechert; Sybille Beier; Walter Elger, all of Berlin, Fed. Rep. of Germany; James R. Bull, Pretoria, South Africa; Günter Neef, Berlin, Fed. Rep. of Germany

[73] Assignee: Schering Aktiengesellschaft, Berlin and Bergkamen, Fed. Rep. of Germany

[21] Appl. No.: 679,043

[22] PCT Filed: Nov. 10, 1989

[86] PCT No.: PCT/DE89/00712
§ 371 Date: May 13, 1991
§ 102(e) Date: May 13, 1991

[87] PCT Pub. No.: WO90/05139
PCT Pub. Date: May 17, 1990

[30] Foreign Application Priority Data

Nov. 11, 1988 [DE] Fed. Rep. of Germany ....... 3838779

[51] Int. Cl.⁵ .................. A61K 31/05; C01J 53/00
[52] U.S. Cl. .................. 514/182; 552/510; 552/530
[58] Field of Search ........ 552/630, 629, 510; 514/182

[56] References Cited

U.S. PATENT DOCUMENTS 4,789,671 12/1988 Bull et al. .................. 514/182

Primary Examiner—Howard T. Mars
Assistant Examiner—Kimberly J. Kestler
Attorney, Agent, or Firm—Millen, White & Zenalo

[57] ABSTRACT

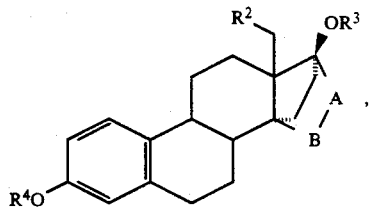

(a)

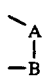

(II)

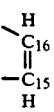

(III)

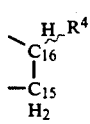

New 14α,17α-ethano-estratrienes of general formula (I) wherein $R^1$ is a hydrogen atom, an alkyl or acyl group with 1 to 12 carbon atoms, $R^2$ is a hydrogen atom or a methyl group, $R^3$ is a hydrogen atom or an acyl group with 1 to 12 carbon atoms and (a) is either (II) or (III), where $R^4$ is an alkyl residue in the α or β position with 1 to 8 carbon atoms or an α,β-alkenyl residue which may contain several double bonds or an α,β-alkinyl residue, both with 2 to 8 carbon atoms, are described. Also described is a process for producing them. These new compounds have a marked oestrogenic activity.

7 Claims, No Drawings

14α,17α-ETHANOESTRATRIENES

This invention relates to 14alpha,17alpha-ethanoestratrienes of general formula I

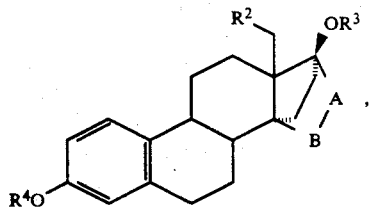

in which
R[1] means a hydrogen atom, an alkyl or acyl group with 1 to 12 carbon atoms,
R[2] means a hydrogen atom or a methyl group,
R[3] means a hydrogen atom or an acyl group with 1 to 12 carbon atoms and $$\begin{array}{c} \diagdown_A \\ | \text{ either} \\ -B \end{array} \quad \begin{array}{c} \diagdown \quad H \\ C_{16} \\ \| \\ -C_{15} \\ H \end{array} \text{ or } \begin{array}{c} \diagdown \quad H \quad \diagup R^4 \\ C_{16} \\ | \\ -C_{15} \\ H_2 \end{array}$$

and R[4] is an alpha- or beta-position alkyl radical with 1 to 8 carbon atoms or an alpha,beta-alkenyl radical or an alpha,beta-alkinyl radical, optionally exhibiting several double bonds, both radicals with 2 to 8 carbon atoms.

Further, the invention relates to a process for the production of compounds of general formula I, pharmaceutical preparations, which contain compounds of general formula I as well as the use of the compounds according to the invention for fertility control of women as well as for treatment of estrogen deficiency symptoms of women.

As acyl groups R[1] and R[3,] radicals of organic carboxylic acids with 1 to 12 carbon atoms are suitable. They are derived from aliphatic, cycloaliphatic, aliphatic-cycloaliphatic, cycloaliphatic-aliphatic and aromatic and aromatic-aliphatic monocarboxylic acids, preferably those acids that are derived from hydrocarbons. The number of carbon atoms in the cycloaliphatics varies from 3 to 7, the phenyl as well as the naphthyl radical can be mentioned as aromatics.

As radicals R[1] and R[3] for the acyl groups the acetic, propionic, butyric, isobutyric, pivalic, caproic, acrylic, crotonic, heptylic, caprylic, pelargonic, decanoic, undecanoic, dodecanoic, 3-cyclopentylpropionic and benzoic acid are preferred.

If R[1] stands for an alkyl group, in this case alkyl radicals, optionally with one or more unsaturations, with 1 to 12 carbon atoms are suitable. R[1] can thus be an alkyl, alkenyl or alkinyl radical with up to 12 carbon atoms. Especially to be mentioned are all alkyl radicals corresponding to the acyl groups mentioned for R[1] and R[3]. The methyl group is especially preferred.

A hydrogen atom is the preferred radical for R[2].

For the fragment

there can stand either a C15-C16 double bond or C15-C16 alkylene group

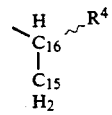

which is substituted in the 16 position with an alpha- or beta-position alkyl radical or an optionally repeatedly unsaturated alk-1,2-enyl radical with 1 to 8 or 2 to 8 carbon atoms. They are especially the methyl, ethyl, propyl, isopropyl, propenyl, butyl, t-butyl, butadienyl, cyclopentylmethyl and cyclopentylmethylene as well as the hexyl group, of which the methyl group can be mentioned as preferred.

Finally a straight-chain alk-1,2-inyl group with 2 to 8 carbon atoms is suitable as substituent R[4]. The ethinyl and propionyl group are preferred.

14alpha,17alpha-etheno-bridged steroids are described in J. Chem. Soc., Chex. Commun., 1986, 451-453 and 14alpha,17alphaetheno-bridged and 14alpha,17alpha-ethano-bridged steriods in international patent application PCT/DE87/00361 as the compounds coming closest &o the compounds of the general formula I, with the same substituents in 3 and 17 position as the compounds according to the invention; in 13 position the known compounds exhibit a methyl group. While the compounds of general formula I present here exhibit the C15-C16 double bond or the alkyl radical on the C-16 atox in the upper ring of the steroid skeleton, the C15-C16 double bond or the C-16 alkyl substituent in/on the lower D ring of the steroid skeleton is in the same arrangement (in each base beta) of the 17 OR substituent (R=H, acyl). In other words, with the present compounds of formula I 14alpha,17alphaethanoestratrienes (A) or 14alpha,17alpha-ethano-16-alkylestratrienes (B) are involved, while with the already known compounds 14alpha,17alpha-ethenoestratrienes (C) or 14alpha,17alpha-alkylethano estratrienes (D) are involved:

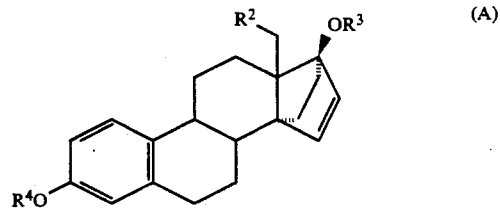

(A)

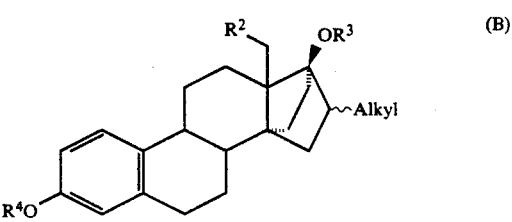

(B)

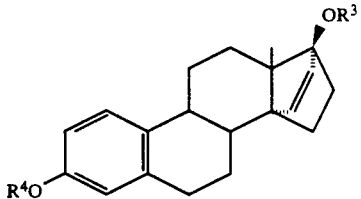

(C)

ered as a threshold value, at which 50% of the animals reach stage 3.

The results of the Allen-Doisy test with 14alpha,17alphaethano-1,3,5(10),15-estratetraene-3,17beta -diol as test compound as well as 14alpha,17alpha-ethano-1,3,5(10)estratriene-3,17beta-diol and estradiol as comparison compounds are summarized in table 1. The uterus weights are determined after autopsy of those animals on which vaginal smears had previously been made.

TABLE 1

Vaginal smear test according to Allen and Doisy (A 1.1 modified) on rats with s.c. administration.
Injection: 1× on d1; autopsy d5, n = 6/group: control n = 12

| Treatment | | Difference body weight d5 − d1 (g) Mean | SD | Uterus weight (moist)[1] Mean | SD | (dry)[1] Mean | SD | Uterus weight (mg)/100 g Kg (moist) Mean | SD | (dry) Mean | SD | Smears n = pos./ n = trt. |
|---|---|---|---|---|---|---|---|---|---|---|---|---|
| 14alpha,17alpha-ethano- | /3,00 ug | −0.33 | 3.56 | 713.92 | 368.43 | 135.83 | 54.62 | 335.57 | 156.29 | 64.61 | 23.10 | 6/6 |
| 1,3,5(10),15-estratetraene- | /1,00 ug | 6.50 | 2.59 | 415.62 | 250.80 | 77.23 | 37.73 | 199.21 | 129.50 | 36.92 | 19.64 | 6/6 |
| 3,17beta-diol | /0,30 ug | 11.50 | 2.26 | 238.45 | 25.65 | 44.93 | 3.84 | 110.19 | 14.62 | 20.74 | 2.21 | 6/6 |
| | /0,10 ug | 16.50 | 6.98 | 156.62 | 10.85 | 29.23 | 2.76 | 70.72 | 6.58 | 13.22 | 1.70 | 6/6 |
| | /0,03 ug | 18.17 | 4.75 | 128.07 | 17.22 | 25.38 | 5.28 | 58.89 | 6.68 | 11.65 | 2.17 | 0/6 |
| 14alpha,17alpha-ethano- | /3,00 ug | 0.67 | 6.86 | 576.37 | 248.15 | 92.98 | 21.53 | 276.18 | 113.26 | 44.81 | 10.05 | 6/6 |
| 1,3,5(10)-estratrien- | /1,00 ug | 2.83 | 4.83 | 327.72 | 37.87 | 66.87 | 13.52 | 158.32 | 23.83 | 32.38 | 7.77 | 6/6 |
| 3,17beta-diol | /0,30 ug | 11.33 | 3.56 | 299.50 | 71.34 | 45.72 | 6.04 | 135.06 | 34.94 | 20.50 | 2.28 | 6/6 |
| | /0,10 ug | 10.83 | 2.79 | 191.80 | 105.71 | 28.18 | 5.62 | 89.92 | 51.58 | 13.14 | 2.58 | 5/6 |
| | /0,03 ug | 17.33 | 3.72 | 134.80 | 41.83 | 24.18 | 3.13 | 60.90 | 22.05 | 10.83 | 1.51 | 2/6 |
| estradiol | /3,00 ug | 7.67 | 5.28 | 367.28 | 108.65 | 71.65 | 14.70 | 170.30 | 49.06 | 33.38 | 7.18 | 6/5 |
| | /1,00 ug | 5.17 | 2.23 | 234.77 | 21.88 | 59.55 | 19.30 | 111.65 | 9.93 | 28.42 | 9.49 | 6/6 |
| | /0,30 ug | 12.00 | 2.10 | 192.10 | 40.03 | 42.18 | 17.18 | 89.32 | 18.90 | 19.57 | 8.01 | 6/6 |
| | /0,10 ug | 14.33 | 3.56 | 137.05 | 17.94 | 25.07 | 3.50 | 61.85 | 9.30 | 11.27 | 1.44 | 6/6 |
| | /0,03 ug | 20.17 | 4.75 | 123.17 | 13.29 | 23.60 | 4.98 | 54.85 | 5.67 | 10.52 | 2.32 | 0/6 |
| Control | | 21.08 | 4.25 | 123.72 | 20.19 | 27.58 | 6.09 | 54.20 | 11.27 | 12.09 | 3.11 | 0/12 |

(M ± SD - p less than 0.05 vs. control, LSD - test)
As other compounds, 14alpha,17alpha-ethano-1,3,5(10)-estratriene-16alpha-ethinyl-3,17beta-diol was tested; at a dose of 0.3 micrograms/d s.c. all 6 examined animals show positive smears.

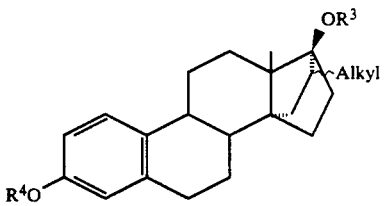

(D)

Further, from PCT/DE87/00361 it comes out that the 14alpha,17alpha-ethenoestratrienes of type C can be hydrogenated to the also strongly estrogen-effective corresponding 15,16-dihydro compounds.

Like the compounds belonging to the prior art, the compounds according to the invention are distinguished by an extraordinarily strong estrogenic effectiveness. In the Allen-Doisy test after subcutaneous administration they are as strongly estrogenically effective as ethinylestradiol and of comparable effectiveness as the already known compounds of type (C).

In the Allen-Doisy test, an evaluation of vaginal smears in ovariectomized rats is performed on days 3, 4, 5 and 8 after the single administration of the test substance. The following cycle stages are distinguished:

1=diestrus (leukocytes and nucleated epithelial cells),
2=proestrus (nucleated epithelial cells),
3=estrus (denucleated horny plaques),
4=metestrus (denucleated horny plaques, leukocytes, epithelial cells).

After oral or subcutaneous administration, estrogenically effective substances result in the proliferation of the vaginal epithelium and in the cornification of surface cell layers. That amount of an estrogen is considered as a threshold value, at which 50% of the animals reach stage 3.

It is surprising that the compounds according to the invention, which contain no 17alpha-ethinyl group, are at least as effective as ethinylestradiol. Ethinylestradiol is still the most often used estrogen in oral treatment.

In comparison with ethinylestradiol, the compounds according to the invention offer the advantage that they exhibit no 17betahydroxy group, which could cause undesirable metabolic reactions.

As is still to be explained, moreover they can be produced by a substantially simpler process than the structurally close compounds of type (C).

Thus, the invention also relates to compounds of general formula I for use in the treatment of estrogen deficiency symptoms and for fertility control in women.

The compounds according to the invention can be formulated and used in the same way as ethinylestradiol. They are processed according to methods known in the art into the usual pharmaceutical agent forms with the additives, vehicles and/or taste corrigents usual in galenic pharmacy. For oral administration, tablets, coated tablets, capsules, pills, suspensions or solutions are especially suitable. For parenteral administration, oily solutions, such as, for example, sesame oil or castor oil solutions, are especially suitable, which can optionally contain in addition another diluent, such as, for example, benzyl benzoate or benzyl alcohol.

The active ingredient concentration in the pharmaceutical compositions is dependent on the form of administration and the field of use. Thus, for example, for the treatment of estrogen deficiency symptoms, capsules or tablets can contain 0.001 to 0.05 mg of active ingredient, oily solutions for intramuscular injection per 1 ml approximately 0.01 to 0.1 mg of active ingredient and vaginal ointments about 0.1 to 10 mg per 100 ml of ointment. For contraception in women, the estrogens according to the invention can be used in combination with gestagens. Tablets or coated tablets for daily intake of a tablet or a coated tablet are to contain preferably 0.003 to 0.05 mg of the estrogen according to the invention and 0.05 to 0.5 mg of a gestagen.

The compounds according to the invention can be used in the case of estrogen deficiency symptoms of women, such as, for example, amenorrhea, dysmenorrhea, sterility, frigidity, endometritis, colpitis and menopausal symptoms. Further, the compounds can be used as estrogenic components in compound preparations with gestagens for fertility control in women.

The new compounds of general formula I

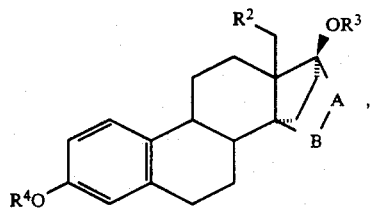 (I)

in which $R^1$, $R^2$ and $R^3$ and

have the meaning already indicated, are produced so that a) if 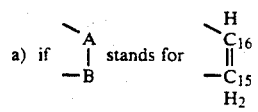 stands for a compound of general formula IIIa

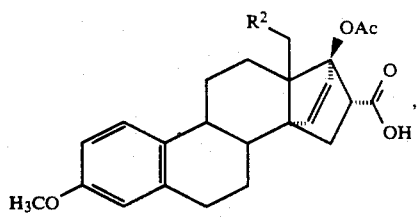 (IIIa)

in which $R^2$ has the meaning indicated in formula I is first hydrogenated and then decarboxylated and oxidized to a compound of general formula II'a

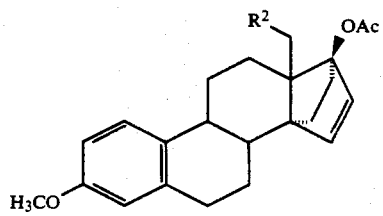 (II'a)

b) or if 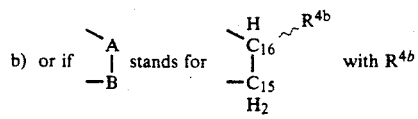 stands for with $R^{4b}$ meaning a methyl group, a compound of general formula IIIb

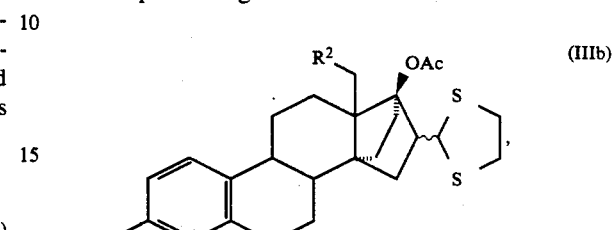 (IIIb)

in which $R^2$ has the meaning already indicated, is reduced to a compound of general formula II'b

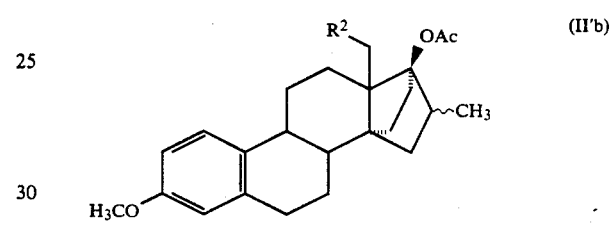 (II'b)

c) or if 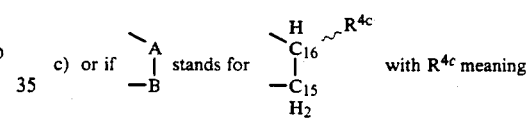 stands for with $R^{4c}$ meaning an alkyl radical or an alpha,beta-alkenyl radical, both with 2 to 8 carbon atoms, optionally exhibiting several double bonds a compound of general formula IIIc

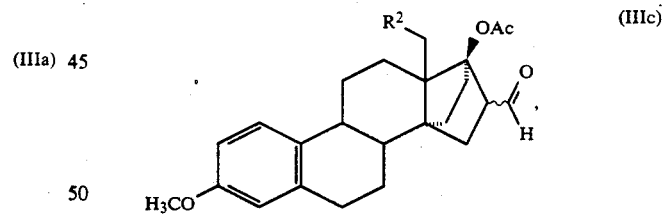 (IIIc)

in which $R^2$ has the meaning already indicated, is reacted with an appropriate Wittig reagent to a compound of general formula II''c

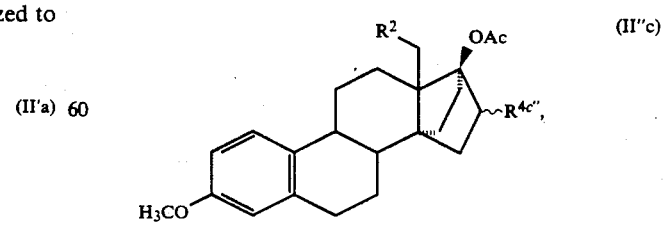 (II''c)

in which $R^{4c''}$ represents an alpha,beta-alkenyl radical, with 2-8 carbon atoms, optionally exhibiting several double bonds the compound of general formula II″c optionally is hydrogenated to a compound of general formula II′c

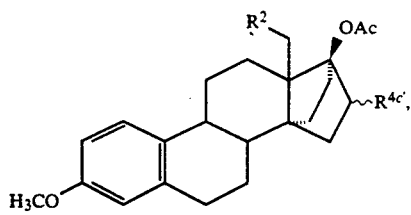

in which $R^{4c'}$ represents an alkyl radical with 2 to 8 carbon atoms,

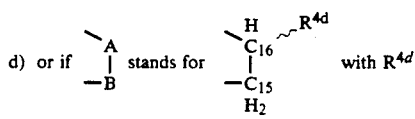

meaning an alpha,beta-alkinyl radical with 2 to 8 carbon atoms, a compound of general formula III c

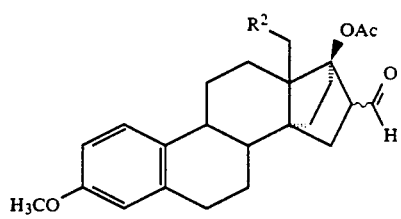

is reacted in a modified Wittig reaction with a mixture of triphenylphosphane and tetrahalomethane CHal₄, and Hal can be bromine and iodine, preferably bromine, to a compound of general formula II″d

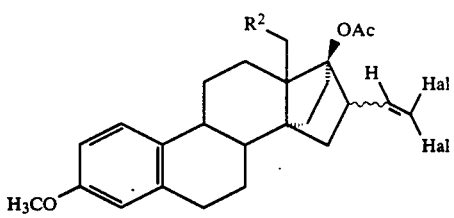

and then in a compound of one of general formulas II′a, II′b, II″c, II′c or II″d optionally the 3-methyl ether is cleaved and if the process variant d) is present, after conversion of the compound of general formula II″d or the corresponding 3-hydroxy compound by cleavage of HHal with a base and halogen/hydrogen exchange and optionally after coupling of the resulting H-ethinyl compound with a linear alkylation reagent exhibiting 1 to 6 carbon atoms to a compound of general formula II′d

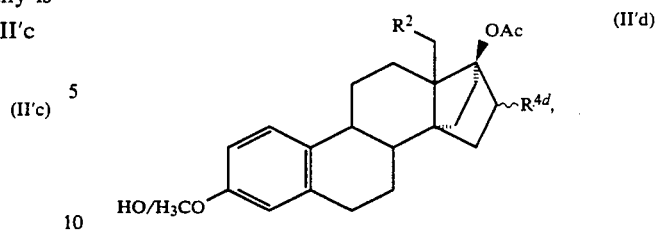

in which $R^{4d}$ has the meaning already indicated and then optionally the released 3-hydroxy group is again etherified and/or the 17-acetoxy group is saponified, optionally the 3- and 17-hydroxy groups are again esterified and optionally a 3,17-diacyloxy compound thus obtained is selectively saponified to the 3-hydroxy-17-acyloxy compound.

Depending on which intermediate or end product of general formulas II′a, II′b, II″c, II′c or II″d (the compounds of these formulas can also be end products of general formula I, if $R^1$ is to be a methyl group and $R^3$ is to be an acetyl group) is desired, different procedures according to the invention are necessary.

a) The D ring is to exhibit a C15–C16 double bond: starting from a 16alpha-carbaldehyde of general formula IVa

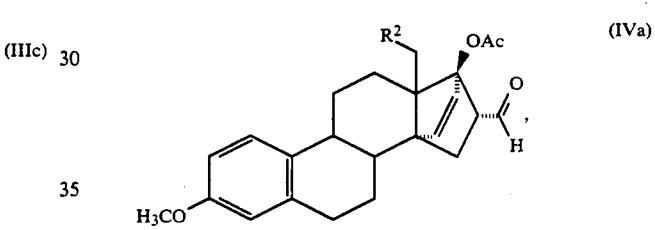

in which $R^2$ stands for an H atom or a methyl group, by oxidation of the carbonyl group, for example with Jones reagent (chromium(VI) oxide/sulfuric acid), the corresponding carboxyl group IIIa is produced.

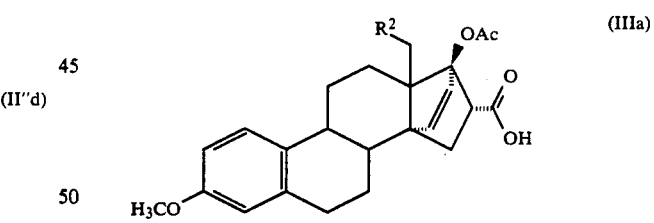

By hydrogenation of the 14alpha,17alpha-etheno bridge, decarboxylation and oxidation (introduction of the C15–C16 double bond) IIIa is converted into a compound of general formula II′a.

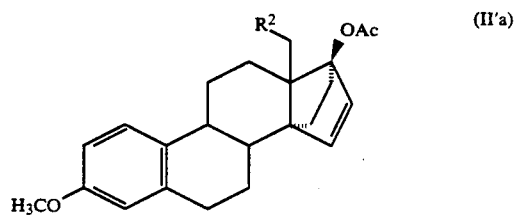

The decarboxylation and oxidation are performed by heating in a solvent under the action of at least one oxidation agent, for example with lead tetraacetate and copper(II) acetate hydrate in benzene or toluene.

b) The D ring is to have a C-16 alpha- or beta-methyl group:

a compound of general formula IIIc

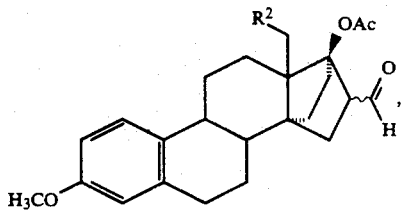
(IIIc)

in which $R^2$ stands for an H atom or a methyl group and the aldehyde function can be in the alpha or beta position, by reaction with 1,2-dimercaptoethane is converted in its ethylene-1,2-dithioketal derivative IIIb;

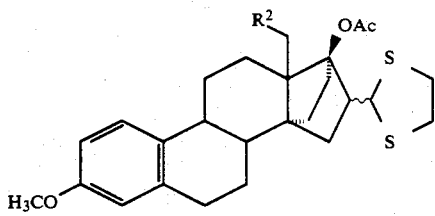
(IIIb)

this compound of formula IIIb is then reduced with a protic solvent to a compound of general formula II'b

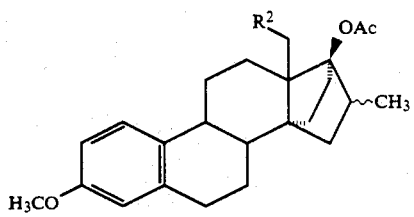
(II'b)

for example, with Raney nickel in alcohol.

c) The D ring is to carry a C16-alpha or beta-alkyl or C-16alpha or beta-alkenyl radical, with 2 to 8 carbon atoms, optionally exhibiting several double bonds:

also starting from an aldehyde of general formula IIIc by a C—C linkage reaction the 16alpha or 16beta-alkenyl or alkyl side chain is synthesized, for example, by Wittig reaction of IIIc with a suitable Wittig reagent, i.e., with a Wittig reagent poorer by one C atom than $R^{4c''}$.

The double bond resulting in the C16 side chain by the Wittig reaction (as well as optionally present in other double bonds) can optionally be again eliminated by hydrogenation.

By the variant described under c) there are achieved both compounds of general formula II''C

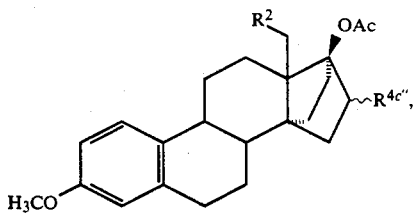
(II'c)

in which $R^{4c''}$ represents at least one simply unsaturated alkenyl radical with 2 to 8 carbon atoms and compounds of general formula II'c

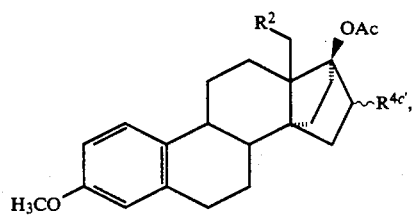
(II'c)

in which now in $R^{4c'}$ the double bonds which were present in $R^{4c''}$ are hydrogenated.

d) The D ring is to exhibit a straight-chain C16 alpha- or C16 beta-alk-1,2-inyl radical with 2 to 8 carbon atoms as substituent:

An aldehyde of formula IIIc as starting product is reacted in a modified Wittig reaction with a mixture of triphenylphosphine and tetrabromomethane or tetraiodomethane. In this case, triphenyl-dibromo (or diiodo) methylene phosphorane functions as reactive species. Then hydrogen bromide or hydrogen iodide is then eliminated from the resulting Wittig reaction product of general formula II''d with a base, such as, for example, n-butyllithium. In the aqueous working up of the reaction product obtained after the elimination, the corresponding 16 alpha- or 16 beta-ethinyl compound is obtained; if after dehydrohalogenation an n-alkylation reagent with 1 to 6 carbon atoms in the alkyl radical is added, compounds of general formula II'd are achieved, in which $R^4$ is an alpha- or beta-position alk-1,2-inyl radical with 3 to 8 carbon atoms. Thus, for example, working up in the presence of methyl iodide leads to the corresponding 16-prop-1,2-inyl compound.

This invention also relates to the compounds of formula IV

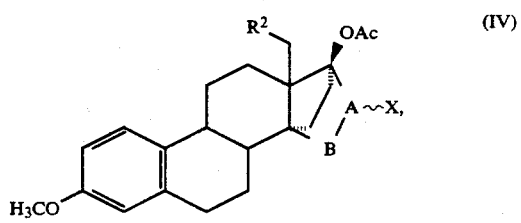
(IV)

in which
$R^2$ stands for a hydrogen atom or a methyl group and either
X means an alpha-position carbaldehyde group

and

A-B means a C—C single bond as well as E-F means a C—C double bond or C—C single bond, or X means a beta-position carbaldehyde group

and A-B and E-F mean two C—C double bonds or two single bonds, since these compounds represent valuable and variously usable intermediate products because of the chemically versatile keto group.

The production of the compounds of general formula IV takes place starting from 3-methoxy-1,3,5(10),14,16-estrapentaen-17-yl acetate ($R^2 = H$)

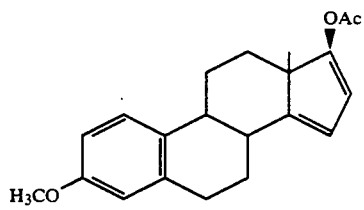

[G. H. Rasmusson et al., Steroids 22, 107, (1973)] or starting from 3-methoxy-1,3,5(10),14,16-estrapentaene-18-methyl-17-yl acetate ($R^2 = CH_3$) by reaction with an unsaturated aldehyde in vicinal position to the keto group. Instructions for preparation of the last-named compound are found in example 16. For example, reaction of the first compound ($R^2 = H$) with acrolein in the cold and in the presence of a Lewis acid yields the [4+2] cyclo adduct

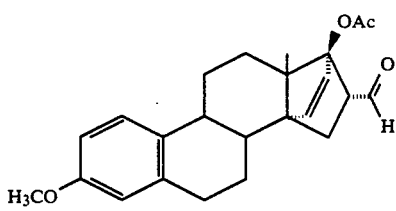

with alpha-position aldehyde function the C16 atom while the [4+2] cyclo adduct with beta-position aldehyde function on the on

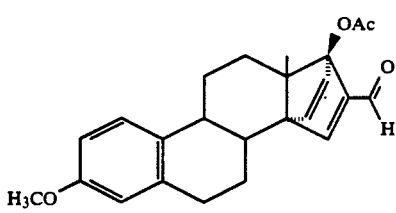

the C16 atom is formed with propinal in the heat. Both cyclo adducts can be catalytically hydrogenated, for example with palladium-activated carbon (also if $R^2 = CH_3$).

Thus the compounds of general formula I according to the invention are distinguished especially by their high estrogenic effectiveness, and they can in addition be produced according to a relatively simple process and easily by the compounds of general formula IVa or IIIc.

The known 14alpha,17alpha-etheno-1,3,5(10)-estratrienes (C) so far have been produced by reduction of the corresponding 16-phenyl sulfones of formula

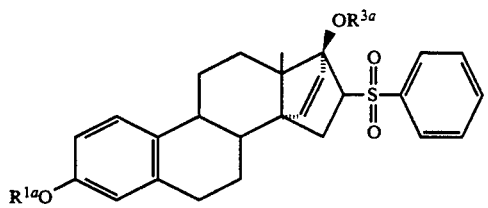

in which $R^{1a} = R^1$ and $R^{3a} = R^3$ or mean precursors of $R^1$ or $R^3$, with an excess of 6% sodium amalgam (J. Chem. Soc.., Chem. Commun. 1986,451–453). For example, for reductive elimination of the phenyl sulfone groups from 2 g of 14alpha,17alpha-etheno-3-methoxy-16alpha-phenylsulfonyl-1,3,5(10) -estratrien-17beta-ol acetate in the usual way 31.5 g of 6% sodium amalgam is necessary, which contains almost 30 g of mercury. For reasons of economy and because of the extreme toxicity of the mercury, such a synthesis cannot be transferred on a reasonable technical scale, since, for example, to reduce 100 kg of the above-named sulfone, 1.5 tons of mercury would be necessary. On the other hand, the present process avoids these disadvantages and damages that occur in dealing with mercury.

Moreover, the compounds of general formula I according to the invention, in which

stands for a C15-C16 double bond, as shown in example 15, can be hydrogenated, by which identical 15,16-dihydro compounds are achieved as by hydrogenation of the known 14alpha,17alpha-ethenoestratrienes of type.C.

This invention is explained in greater detail by the following examples.

EXAMPLE 1

17beta-Acetoxy-14alpha,17alpha-etheno-3-methoxy-1,3,5(10)-estratriene-16alpha-carbaldhyde (2)

10.0 g (30.8 mmol) of 3-methoxy-1,3,5(10),14,16-estra-pentaen-17-yl acetate (1) [G. H. Rasmusson et al., Steroids 22, 107, (1973)] and 4.17 ml (62.7 mmol) of acrolein in 124 ml of toluene were mixed by instillation with ice cooling with 0.19 ml (1.6 mmol) of boron trifluoride etherate in 11.4 ml of toluene. The reaction was stirred for 16 hours at room temperature and then poured onto ice/water. Then it was extracted with ethyl acetate and the organic phase, after washing with sodium bicarbonate solution and water, was dried on sodium sulfate. Filtration and evaporation of the solvent yielded 9.9 g of solid residue. By chromatography on silica gel with ethyl acetate/hexane (1:2→1:1), 8.55 g of (2) with a melting point of 183–185° C. was obtained.

$[\alpha]^{20}D + 102.5°$ (C. 0.120, CHCl$_3$)

EXAMPLE 2

17beta-Acetoxy-14alpha,17alpha-etheno-3-methoxy-1,3,5(10)-estratriene-16alpha-carboxylic acid (3)

8.0 g (21.0 mmol) of 2 in 180 ml of acetone was mixed by instillation with 11.0 ml (29.3 mmol) of Jones reagents (2.67 g of chromium(VI) oxide in 7.7 ml of water and 2.3 ml conc. sulfuric acid) at 0° C. The reaction mixture was stirred for 3 ½ hours with ice cooling and 1 hour at room temperature and then poured onto ice/water. Then it was extracted with ethyl acetate, the organic phase was washed with water and dried on sodium sulfate. Filtration and removal of solvent yielded 8.03 g of (3) with a melting point of 194–198° C.

EXAMPLE 3

17beta-Acetoxy-14alpha,17alpha-ethano-3-methoxy-1,3,5(10)-estratriene-16alpha-carboxylic acid (4)

8.0 g of (3) was hydrogenated in 672 ml of ethanol in the presence of 1.76 g of Pd-C (10%) at standard pressure. After filtration and evaporation of the solvent, 7.5 g of (4) was obtained as crude product with a melting point of 224–227° C.

EXAMPLE 4

14alpha,17alpha-Ethano-3-methoxy-1,3,5(10),15-estratetraen-17beta-ol acetate (5)

7.45 g (18.7 mmol) of (4) and 0.65 (3.26 mmol) of copper(II) acetate hydrate were stirred in 1.5 ml of pyridine and 137 ml of benzene first for 30 minutes at room temperature and after addition of 13.5 g (30.4 mmol) of lead tetraacetate at 90° C. were stirred for 4 hours in a nitrogen atmosphere with exclusion of light. The reaction mixture was filtered through silica gel, rewashed with 2 liters of ethyl acetate/hexane (1:1) and the filtrate was concentrated by evaporation. By chromatography of the oily residue on silica gel with ethyl acetate/hexane (1:1), 1.27 g of (5) was obtained as bright yellow oil, additionally 1.16 g was contaminated.

EXAMPLE 5

14alpha,17alpha-Ethano-1,3,5(10),15-estratetraene-3,17beta-diol (6)

1.18 g (3.35 mmol) of (5) in 354 ml of toluene was refluxed with 88.5 ml (106.2 mmol) of diisobutylaluminium hydride (1.2 molar in toluene) for 14 hours in a nitrogen atmosphere. The cooled reaction mixture was poured on ice/dilute acetic acid. Then it was extracted with ethyl acetate and the organic phase, after washing with sodium bicarbonate solution and water, was dried on sodium sulfate. After filtration and evaporation of the solvent, 1.3 g of solid was obtained, which after chromatography on silica gel with hexane—hexane/ethyl acetate (1:1) yielded 540 mg of (6) with a melting point of 200° C.
$[\alpha]^{20}D-11.4°$ (C 0.105 CHCl$_3$).

EXAMPLE 6

17beta-Acetoxy-14aloha,17aloha-ethano-3-methoxy-1,3,5(10)-estratriene-16alpha-carbaldhyde (7)

2.0 g of (2) in 250 ml of ethyl acetate was hydrogenated with 0.5 g of Pd-C (10%) at standard pressure. After removal of the catalyst and evaporation of the solvent, 1.99 g of (7) with a melting point of 151–152° C. was obtained.

EXAMPLE 7

16alpha-(1,3-Dithiolan-2-yl)-14aloha,17alohaethano-3-methoxy-1,3,5(10)-estratrien -17beta-ol acetate (8)

6.51 g (17.0 mmol) of (7) and 2.26 ml (26.9 mmol) of 1,2-dimercaptoethane were dissolved in 15 ml of methylene chloride and mixed with instillation at 0°0 C. with 0.6 ml (4.76 mmol) of boron trifluoride etherate in 5.9 ml of methylene chloride at 0° C. The reaction mixture was stirred for 3 more hours at room temperature, diluted with ethyl acetate and washed with 5% sodium hydroxide solution and water. Drying of the organic phase on sodium sulfate, filtration and evaporation of the solvent yielded 7.62 g of crude product of (8), which is used for Raney nickel desulfurization.

EXAMPLE 8

14aloha,17alpha-Ethano-3-methoxy-1,3,5(10)-estratriene-16alphamethyl-17beta-ol acetate (9)

7.52 g of (8) was refluxed in 400 ml of ethanol together with about 15 g of Raney nickel in a nitrogen atmosphere. After filtration and removal of the solvent 5.60 g of (9) with a melting point of 115° C. was obtained.

EXAMPLE 9

14alpha,17alpha-Ethano-16aloha-methyl-1.3.5(10)-estratriene3,17beta-diol (10)

2.0 g (5.42 mmol) of (9) was refluxed with 75.0 ml (91.4 mmol) of diisobutylaluminum hydride (1.2 molar in toluene) for 5 ½ hours under nitrogen. The cooled reaction mixture was diluted with toluene and poured onto ice/dilute acetic acid. After addition of common salt, it was extracted with ethyl acetate and the organic phase was washed with sodium bicarbonate solution and water. After drying on sodium sulfate, filtration and after removal of the solvent, 1.71 g of solid was obtained. Recrystallization in acetone/hexane yielded 610 mg of (10) with a melting point of 264–265° C.
$[\alpha]^{20}D+30.4°$ (C 0.105; CHCl$_3$).

EXAMPLE 10

17beta-Acetoxy-14aloha,17aloha-etheno-3-methoxy-1.3.5(10),15-estratetraene-16-carbaldhyde (11)

10.0 g (30.8 mmol) of (1) and 28.21 g of a mixture of propinal, 2-butanone and diethyl ether [produced according to M.G. Valiev et. al. Synthesis 461 (1960); batch:36.5 g (0.65 mmol) of propargyl alcohol; the product after working up according to instructions still contains 2-butanone and diethyl ether] in 114 ml of toluene were refluxed for 10 hours. The cooled reaction mixture was concentrated by evaporation (15.57 g of crystallizing oil) and recrystallized in ethyl acetate/hexane. 7.84 g of (11) with a melting point of 155.5° C. was obtained.
$[\alpha]^{20}D-52.3°$ (C 0.105; CHCl$_3$).

EXAMPLE 11

17beta-Acetoxy-14alpha,17alpha-ethano-3-methoxy-1,3,5(10)-estratriene-16beta- carbaldhyde (12)

2.0 g of (11) was hydrogenated with 400 mg of Pd-C (10%) in 40 ml of ethyl acetate at standard pressure. After filtration and removal of the solvent, 2.06 g of solid remained.. The crude product—according to $^1$H-NMR consisting of 85% 16beta- and 15% 16alpha-carbaldhyde—is used for thioketalation.

EXAMPLE 12

16beta-(1.3-Dithiolan-2-yl)-14aloha,17alpha-ethano-3-methoxy-1,3,5(10)-estratrien -17beta-ol acetate (13)

3.0 g (7.84 mmol) of (12) and 1.04 ml (12.4 mmol) of 1,2-dimercaptoethane are dissolved in 7 ml of methylene chloride and mixed by instillation at 0° C. with 0.28 ml (2.20 mmol) of boron trifluoride etherate in 2.7 ml of methylene chloride. The reaction mixture was stirred for 20 minutes at 0° C. and 3 hours at room temperature. After dilution with ethyl acetate, the reaction mixture was washed with 5% sodium hydroxide solution and water. The organic phase was dried on sodium sulfate, filtered and evaporated to dryness. 3.06 g of (13) was obtained as crude product, which was used for Raney nickel desulfurization.

EXAMPLE 13

14alpha,17alpha-Ethano-3-methoxy-1,3,5(10)-estratriene-16beta-methyl-17beta-ol acetate (14)

3.0 g of (13) was refluxed together with about 7.5 g of Raney nickel in 200 ml of ethanol under protective gas. After cooling, filtration and evaporation of the solvent, 2.40 g of colorless oil was obtained, which then is reacted with diisobutylaluminum hydride.

EXAMPLE 14

14alpha,17alpha-Ethano-16beta-methyl-1,3,5(10)-estratriene-3,17beta-diol (15)

2.22 g (6.02 mmol) of (14) was refluxed with 84.4 ml (101.2 mmol) of diisobutylaluminum hydride (1.2 molar in toluene) for 5 hours under inert gas. The reaction mixture was worked up analogously to (10). After drying, 1.70 g of solid was obtained, which after chromatography on silica gel with toluene → toluene/ethyl acetate (4:1) yielded 355 mg of (15) with a melting point of 233° C.

$[\alpha]^{20}D + 82.0°$ (C 0.1; $CHCl_3$).

EXAMPLE 15

14alpha,17alpha-Ethano-1,3,5(10)-estratriene-3,17beta-diol (16)

200 mg (0.675 mmol) of (6]in 25 ml of ethanol was hydrogenated in the presence of 50 mg of Pd-C (10%) at standard pressure. After filtration and evaporation of the solvent, 200 mg of (16) with a melting point of 227-230° C. was obtained as crude product.

EXAMPLE 16

17beta-Acetoxy-16aloha-(2,2-dibromovinyl)-14aloha,17aloha-ethano-3-methoxy-1,3,5(17)

18.9 g of carbon tetrabromide is added at −10° C. to 7.3 g of 7 and 30.0 g of triphenylphosphine in 583 ml of methylene chloride. The reaction mixture is stirred for 2 more hours at −10° C. and then washed with sodium bicarbonate solution and water. The organic phase is dried on sodium sulfate, filtered and concentrated by evaporation. Filtration of the solid residue (46.3 g) with ethyl acetate/hexane (1:3) through silica gel yields 9.8 g of 17 as crystallizing oil.

EXAMPLE 17

17beta-Acetoxy-16aloha-(2,2-dibromovinyl)-14alpha,17alpha-ethano-3-methoxy-1,3,5(10)-estratrien-3-ol (18)

38.1 ml of a 1 molar solution of boron tribromide in methylene chloride is instilled at −35° C. in 9.5 g of 17 in 229 ml of methylene chloride. After 4 hours stirring at 0° C. the reaction mixture is mixed with ice water and with methylene chloride. The organic phase is washed with water and dried on sodium sulfate. After filtration and removal of the solvent, 9.2 g of 18 is obtained as bright yellow foam.

EXAMPLE 18

16aloha-Ethinyl-14alpha,17aloha-ethano-1,3,5(10)-estratriene-3,17beta-diol (19)

4.0 g of 18 in 73 ml of tetrahydrofuran is mixed with instillation at −78° C. under nitrogen with 28.6 ml of a 1.6 molar solution of butyllithium in tetrahydrofuran. After 3.5 hours stirring at −78° C 100 ml of saturated ammonium chloride solution is added to the reaction mixture. After heating to room temperature it is extracted with ethyl acetate and the organic phase is washed with water. After drying on sodium sulfate, filtration and evaporation of the solvent, 3. g of solid accumulates, which after chromatography on silica gel with ethyl acetate/hexane (1:2) yields 1.4 g of solid. After recrystallization in isopropanol 380 mg of 19 with a melting point of 226-228° C. is obtained.

EXAMPLE 19

3-Methoxy-1,3,5(10),14,16-estra-pentaene-18-methyl-17-yl acetate 2.5 g of 18beta-ethyl-3-methoxygona-1,3,5(10),14-tetraen-17-one (produced according to US patent 3,577,410) and 1.0 g of p-toluenesulfonic acid anhydride are refluxed in a mixture of 25 ml of acetic anhydride and 25 ml of isopropenyl acetate for 8 hours. For working up, the reaction mixture obtained was poured into ice water and then pyridine was added. It was stirred for 2 more hours, taken up in ethyl acetate, washed neutral with sodium bicarbonate and common salt solution and dried on sodium sulfate. Removal of the solvent in a vacuum yielded 2.4 g of crude product, whose further purification [HPLC, reversed phase, 600 ml column, eluent hexane/ethyl acetate (0→30% ethyl acetate)] yielded 800 mg of the title compound with a melting point of 120° C.

We claim:

1. A 14α,17α-ethanoestratriene of formula I

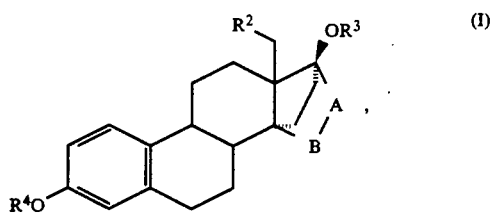

wherein
$R^1$ is H or a $C_{1-12}$-alkyl or -acyl group,
$R^2$ is H or a methyl group,
$R^3$ is H or a $C_{1-12}$-acyl group, and

is either

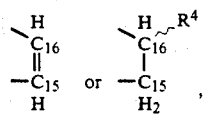

wherein is an α- or β-position $C_{1-8}$-alkyl radical or a $C_{2-8}$-α,β-alkenyl radical or a $C_{2-8}$-α,β-alkinyl radical optionally having additional double bonds.

2. A compound of claim 2 which is

14α,17α-Ethano-1,3,5(10),15-estratetraene-3-17β-diol;

14α,17α-ethano-16α-methyl-1,3,5(10)-estratriene-3,17β-diol;

14α,17α-ethano-16β-methyl-1,3,5(10)-estratriene-3,17β-diol;

14α,17α-ethano-3-methoxy-1,3,5(10),15-estratetraen-17β-ol acetate;

14α,17α-ethano-3-methoxy-1,3,5(10)-estratriene-16α-methyl-17β-ol acetate;

14α,17α-ethano-3-methoxy-1,3,5(10)-estratriene-16β-methyl-17β-ol acetate; or

16α-ethinyl-14α,17α-ethano-1,3,5(10)-estratriene-3,17β-diol.

3. 14α,17α-Ethano-1,3,5(10),15-estratetraene-3,17β-diol, a compound of claim 1.

4. A pharmaceutical preparation comprising an effective amount of a compound of claim 1 and a pharmaceutically acceptable excipient.

5. A pharmaceutical preparation comprising an effective amount of a compound of claim 2 and a pharmaceutically acceptable excipient.

6. A method of controlling fertility, comprising administering an effective amount of a compound of claim 1.

7. A method of treating estrogen deficiency symptoms in a woman in need of such treatment, comprising administering an effective amount of a compound of claim 1.

* * * * *

UNITED STATES PATENT AND TRADEMARK OFFICE
CERTIFICATE OF CORRECTION

PATENT NO. : 5,134,136

DATED : July 28, 1992

INVENTOR(S) : Gerald KIRSCH et al.

It is certified that error appears in the above-identified patent and that said Letters Patent is hereby corrected as shown below:

CLAIM 1; col. 17; Line 7:

after "wherein" insert $R^4$

Signed and Sealed this

Seventh Day of September, 1993

Attest:

BRUCE LEHMAN

Attesting Officer   Commissioner of Patents and Trademarks